(12) United States Patent
Stihl

(10) Patent No.: US 6,508,811 B2
(45) Date of Patent: Jan. 21, 2003

(54) FASTENING ELEMENT FOR A MEDICAL INSTRUMENT AND SUCH MEDICAL INSTRUMENT

(75) Inventor: Ewald Stihl, Geisingen (DE)

(73) Assignee: Karl Storz GmbH & Co. KG (DE)

( * ) Notice: Subject to any disclaimer, the term of this patent is extended or adjusted under 35 U.S.C. 154(b) by 129 days.

(21) Appl. No.: 09/817,078

(22) Filed: Mar. 26, 2001

(65) Prior Publication Data

US 2001/0014789 A1 Aug. 16, 2001

Related U.S. Application Data

(63) Continuation of application No. PCT/EP00/07205, filed on Jul. 26, 2000.

(30) Foreign Application Priority Data

Jul. 26, 1999 (DE) .......................................... 199 35 012

(51) Int. Cl.[7] .......................... A61B 17/00; A61B 17/34
(52) U.S. Cl. .......................... 606/1; 600/185; 600/193; 600/196; 600/102; 403/388
(58) Field of Search ................................ 600/185, 187, 600/190, 194, 197, 120, 125, 102, 104, 193, 196, 114; 403/388, 362; 601/1

(56) References Cited

U.S. PATENT DOCUMENTS

| 2,630,835 | A | | 3/1953 | Russel |
| 4,562,832 | A | | 1/1986 | Wilder et al. .................. 128/20 |
| 4,744,361 | A | | 5/1988 | Karasawa ............... 128/303.15 |
| 4,867,404 | A | * | 9/1989 | Harrington et al. .......... 600/102 |
| 5,143,054 | A | | 9/1992 | Adair ........................... 128/18 |
| 5,379,755 | A | | 1/1995 | Heckele ......................... 128/4 |
| 5,713,869 | A | | 2/1998 | Morejon ..................... 604/174 |
| 5,876,332 | A | * | 3/1999 | Looney ...................... 600/102 |
| 6,086,530 | A | * | 7/2000 | Mack .......................... 600/125 |

FOREIGN PATENT DOCUMENTS

| DE | 41 19 171 A1 | 1/1992 |
| DE | 41 37 426 C1 | 2/1993 |
| EP | WO89/11305 | 11/1989 |

* cited by examiner

Primary Examiner—Linda C. M. Dvorak
Assistant Examiner—Jocelyn Ram
(74) Attorney, Agent, or Firm—St. Onge Steward Johnston & Reens LLC

(57) ABSTRACT

A fastening element is provided for securing a rod-shaped element to a shaft of a medical instrument. The fastening element comprises a bracket for engaging at least partially the circumference of the rod-shaped element, where the bracket can be inserted into a side opening of the shaft portion. The fastening element further comprises a tensioning mechanism, which when actuated draws the bracket in the direction out of the opening, thereby clamping the rod-shaped element to the shaft portion. The clamping force of the tensioning mechanism for clamping the rod-shaped element is continuously adjustable when actuating the tensioning mechanism.

25 Claims, 4 Drawing Sheets

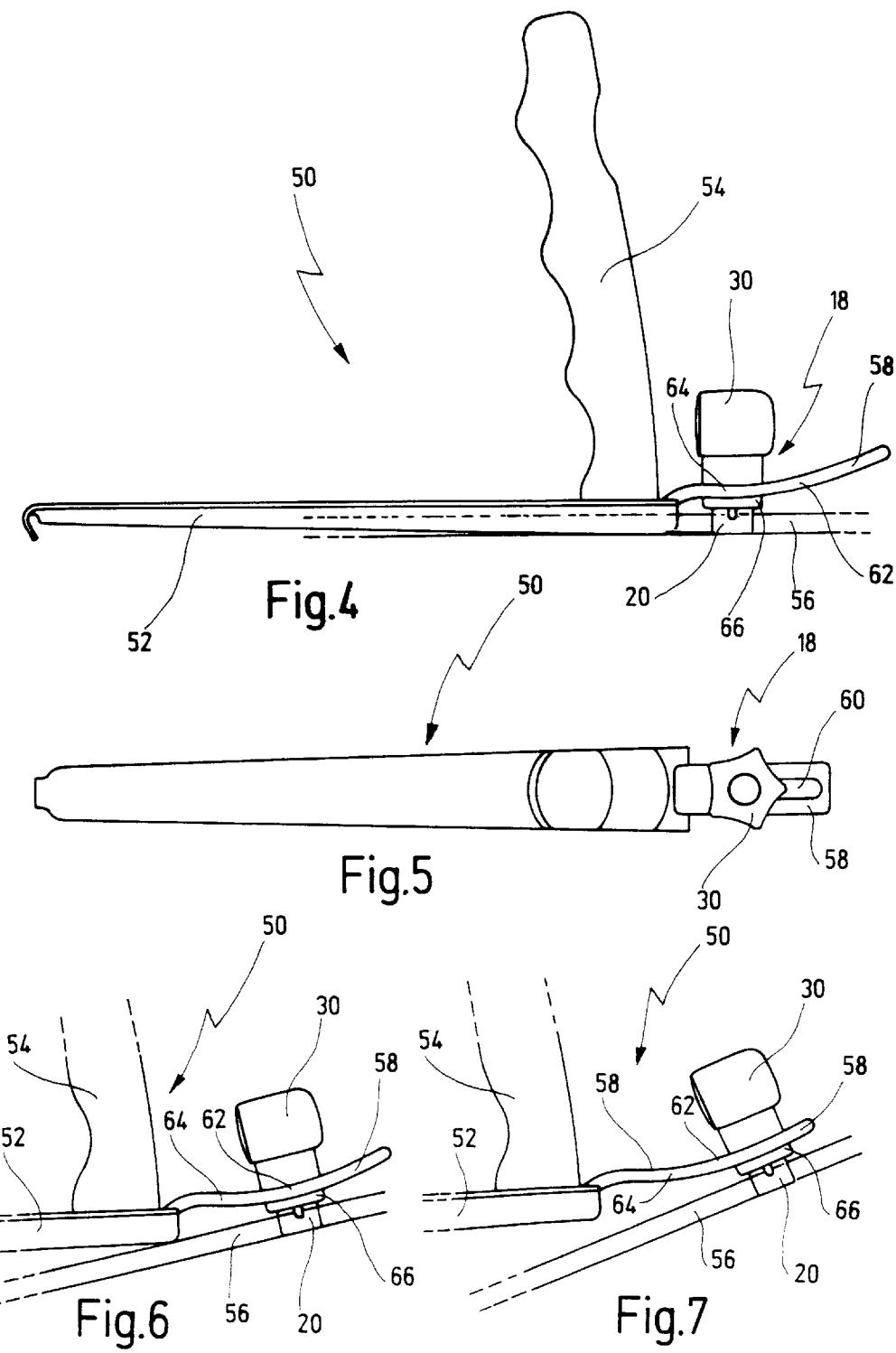

FASTENING ELEMENT FOR A MEDICAL INSTRUMENT AND SUCH MEDICAL INSTRUMENT

CROSS REFERENCE TO PENDING APPLICATION

This application is a continuation of pending International Application PCT/EP00/07205 filed on Jul. 26, 2000 which designates the United States.

BACKGROUND OF THE INVENTION

The invention relates to a fastening element for securing a rod-shaped element to a shaft of a medical instrument. A bracket at least partially engages the circumference of the rod-shaped element, where the bracket can be inserted in a side opening of a portion of the shaft. A tensioning mechanism draws the bracket out of the opening, whereby the rod-shaped element is securely clamped to the shaft portion.

The invention also relates to a medical instrument making use of such a fastening element.

A fastening element and an instrument of the mentioned type are disclosed in the U.S. Pat. No. 5,713,869.

With medical instruments, there is frequently the need to use additional instruments or components, which normally are configured to be substantially rod-shaped, i. e. elongated as the shaft of the instrument itself. This extends the functions of the medical instrument.

A rod-shaped element in the sense of the present invention is for example an irrigation shaft, a shaft for optics or an instrument shaft for a further auxiliary instrument, such as cutters, pincers or a canula, a probe, an electrode support or the like, only to name a few. "Rod-shaped" is to be understood independent of the outer contour and independent of whether the element is hollow (tubular) or is solid.

In the scope of the present invention, the shaft of the medical instrument can be a tubular shaft, for example of a laryngoscope. In such a case, it is desirable that the rod-shaped element be secured to the interior of the shaft, so that the additional rod-shaped element does not block the view or does not enlarge the outer diameter of the tubular shaft of the medical instrument.

In the scope of the present invention, however, the shaft of the medical instrument can also be configured such that the shaft wall is not closed about the periphery as with a tubular shaft, but is open to the side.

The known fastening element of the mentioned U.S. Pat. No. 5,713,869 comprises a bracket, which can be inserted from the outside into the interior of the shaft through a side opening, a movable lever with a cam is provided as a tensioning mechanism for drawing the bracket in the direction out of the shaft. By moving the lever out of a position in longitudinal direction of the fastening element into a position transversely to the longitudinal direction, the cam engages with the outer wall of the shaft and the bracket is drawn outwardly by rolling the cam against the outer wall of the shaft.

The tensioning mechanism of the known fastening element, however, has the drawback that the tensioning mechanism is not variable, so that the known fastening element is suited only for clamping a rod-shaped element with a defined diameter. If a rod-shaped element is used which is too thin, actuating the lever does not draw the bracket far enough out of the opening to securely clamp the rod-shaped element. If the rod-shaped element is too thick, the lever can not be actuated in some circumstances and the bracket can then not be fixed in the tensioned state. In addition, the danger exists with rod-shaped elements of larger diameter that the clamping force when applying the lever is excessive, so that the rod-shaped element is bent or crushed. Especially, when the rod-shaped element contains the endoscope optics, the danger exists that the optics are damaged by excessive clamping forces.

A fastening element is also known from the German Patent DE 41 37 426, which in contrast to the above mentioned fastening element is inserted in longitudinal direction of the instrument shaft into a proximal end opening and is clamped there with a jaw in the manner of a screw clamp. A seat for retaining a rod-shaped element is provided in the fastening element, which includes a leaf spring for clamping the rod-shaped element in the seat. However, this represents insufficient means for clamping the element to the shaft.

The portion of the shaft in which the opening is provided for inserting the bracket can be the wall of the shaft itself according to the present invention or the shaft portion can be formed as a holder connected to the shaft.

The object of the present invention is to provide such a fastening element of the mentioned type with which rod-shaped elements of various cross sections can be securely fastened to a portion of the shaft without damage.

SUMMARY OF THE INVENTION

According to the present invention, this object is achieved by a fastening element for securing a rod-shaped element on a shaft of a medical instrument, comprising a bracket for engaging at least partially a circumference of said rod-shaped element, said bracket being insertable in a side opening of a shaft portion of said shaft; a tensioning mechanism which when actuated draws said bracket in a direction out of said opening for clamping said rod-shaped element onto said shaft portion, wherein said tensioning mechanism is configured such that the clamping force of said tensioning mechanism for clamping said rod-shaped element is continuously adjustable when actuating said tensioning mechanism.

According to the present invention this object is also achieved by a medical instrument, comprising a shaft having at least one side opening in a shaft portion of said shaft, a fastening element for securing a rod-shaped element on said shaft, said fastening element further comprising a bracket for engaging at least partially a circumference of said rod-shaped element, said bracket being insertable in said side opening of said shaft portion of said shaft, a tension mechanism which when actuated draws said bracket in a direction out of said opening for clamping said rod-shaped element onto said shaft portion, wherein said tensioning mechanism is configured such that the clamping force of said tensioning mechanism for clamping said rod-shaped element is continuously adjustable when actuating said tensioning mechanism.

According to the present fastening element, a type of clamping adapter is provided with which a rod-shaped element can be securely clamped to the shaft of a medical instrument with simple handling. The bracket of the fastening element is inserted through the opening in a portion of the shaft, where the rod-shaped element can then be inserted into the bracket. The tensioning mechanism is then actuated and the bracket is continuously drawn in the direction out of the opening in the shaft portion until the rod-shaped or tubular element is clamped to the shaft. Due to the continuous action of the tensioning mechanism, the fastening element is universally applicable to different rod-shaped elements of various cross sectional dimensions. The present fastening element now makes it possible for example to secure a flushing shaft or a shaft for optics. With the present configuration of the fastening element, a high clamping force for securing the rod-shaped element is achieved, however, being adjustable by the hand of the user, so that differently dimensioned rod-shaped elements can be clamped to the portion of the shaft with about the same clamping force. The rod-shaped element does not deform and is not damaged, despite a high clamping force.

The object underlying the present invention is thus completely achieved.

In a preferred embodiment, the tensioning mechanism comprises a screw mechanism comprising an actuator element which is rotatable about a center axis of the fastening element, whose rotary motion is converted into a motion of the bracket in an axial direction of the fastening element.

A tensioning mechanism having a screw mechanism for tightening the bracket has the advantage that the hand force of the user when actuating the tensioning mechanism is well controllable, because the user can easily determine the achieved clamping force through the increasing difficulty in turning the actuator element. In addition, such a screw mechanism can be easily configured to be self-locking, so that the rod-shaped element can not loosen after tightening the bracket.

In a further preferred embodiment, the tensioning mechanism comprises a retainer for the bracket movable in axial direction of the fastening element, to which the bracket is secured and which is connected to the rotatable actuator element through a threading engagement.

The advantage is that a screw mechanism requiring few parts is provided for converting the rotary movement of the actuator element into a translational movement of the bracket, which additionally is self-locking.

In a further preferred embodiment, the fastening element comprises an abutment for substantially form-locking engagement with the contour of the shaft portion.

The advantage is that a particularly high clamping force can be applied for clamping the rod-shaped element to the shaft portion due to the substantially form-locking engagement with the abutment, without damaging the shaft portion through point loads or edges on the fastening element.

In a further preferred embodiment, the tensioning mechanism comprises a turning knob surrounding a first non-rotatable bushing, the bushing compring a base portion provided with an opening for the bracket, whose outer side engages with the shaft portion, the first bushing enclosing the retainer, formed as a second bushing, the turning knob being fixably connected to a pivot pin, extending through the retainer, which is engaged with the retainer through a threading.

This configuration of the present fastening element ensures a reliable function of the fastening element, easy operation and in addition a small size, which is desired for medical instruments. The base portion of the first bushing can be formed as the mentioned abutment in advantageous manner.

In a further preferred embodiment, the bracket comprises a radially elastic retaining section formed to be partially circularly expanded, into which the rod-shaped element can be inserted, the retaining section having a diameter which is larger than the transverse dimension of the opening in the shaft portion.

The feature has the advantage that the fastening element after having been placed in the opening on a portion of the shaft is locally fixed in self-holding manner to the shaft due to the circularly expanded, radially elastic retaining section, this before the rod-shaped element is inserted into the bracket and the bracket tightened down. The fastening element can thus be inserted into the opening of the shaft portion as a type of clip and will not fall out even when the rod-shaped element is not inserted into the bracket. The handling operation of the fastening element for securing the rod-shaped element is therefore substantially improved.

In a further embodiment, the bracket is formed with small material thickness, preferably in the form of a band.

The advantage is that the bracket does not represent an obstacle taking up space, because it does not substantially project radially from the rod-shaped or tubular element.

In a further preferred embodiment, the bracket extends in longitudinal direction of the rod-shaped element over a portion of same.

The advantage is that the rod-shaped element can be secured to the shaft of the instrument even with a single fastening element according to the present invention, without the element being able to pendle or tip. A width of the bracket of about 0.5 to 1 cm is already sufficient, without the invention being limited thereto.

In a further preferred embodiment, a counterplate is provided on the bracket at the side of the opening facing the rod-shaped element.

With such a counterplate, it can be advantageously avoided that the rod-shaped element, when having a very small diameter, is partially drawn into the opening with its outer periphery when tightening the fastening element. The counterplate is preferably configured such that it closes the opening and optionally acts as a form-locking counter-support for the rod-shaped element.

In a preferred embodiment of the instrument, the shaft portion is formed by the wall of the shaft itself.

This can be of advantage for an instrument having a tubular shaft, where the rod-shaped element is to be clamped in the interior of the tubular shaft with the fastening element and where in such a case only an opening needs to be provided in the wall of the tubular shaft in simple constructive manner.

However, it is also preferred when the shaft portion is a holder connected to the shaft.

Such a holder can be fixably connected to the shaft of the instrument or as described in a further preferred embodiment be configured to be secured at different locations on the shaft. The holder element can for example be formed as a clamping member itself with clamping means through which the holder element can be clamped at various locations on the shaft.

In a preferred embodiment, the opening in the shaft portion is configured as a slotted hole, whose axis extends in the longitudinal direction of the shaft.

This has the advantage that the fastening element can be attached at various positions in the longitudinal direction of the shaft of the instrument, so that the rod-shaped element can also be clamped at various positions on the instrument.

In a further preferred embodiment, a plurality of openings distributed on the shaft portion are present.

The advantage is that the rod-shaped element can be secured at various positions on the shaft with the corresponding arrangement of the openings.

In a further preferred embodiment of the instrument, the shaft portion comprises at least partially a curved section which is curved with respect to the longitudinal direction of the shaft, where the opening is formed as a slotted hole and extends at least over the curved section of the shaft portion.

The advantage is that the rod-shaped element can be secured on the shaft at different angular orientations with respect to the longitudinal direction of the shaft. This embodiment is especially suitable for the case that the rod-shaped element contains observation optics. With the different possible angular positions between the optics and the shaft, different view directions can be realised relative to the longitudinal direction of the shaft.

Further advantages can be taken from the following description and the attached drawings. It will be understood that the above mentioned features and those to be discussed below are not only applicable in the given combinations, but may be used in other combinations or taken alone without departing from the scope of the present invention.

Embodiments of the invention are illustrated in the drawings and will be described in more detail below:

BRIEF DESCRIPTION OF THE DRAWINGS

FIG. 4 shows a second embodiment of a medical instrument in side view, where the instrument has a shaft open to the side to which a rod-shaped element is fixed with the fastening element of FIGS. 1 to 3.

FIG. 5 shows a plan view of the instrument in FIG. 4.

FIG. 6 shows a proximal portion of the instrument in FIGS. 4 and 5 where the rod-shaped element is fixed in a different angular position compared to FIG. 4 with respect to the longitudinal direction of the shaft.

FIG. 7 shows an illustration similar to FIG. 6, where the rod-shaped element is fixed at still another angular position with respect to the longitudinal direction of the shaft.

DETAILED DESCRIPTION OF PREFERRED EMBODIMENTS

Figure 1:
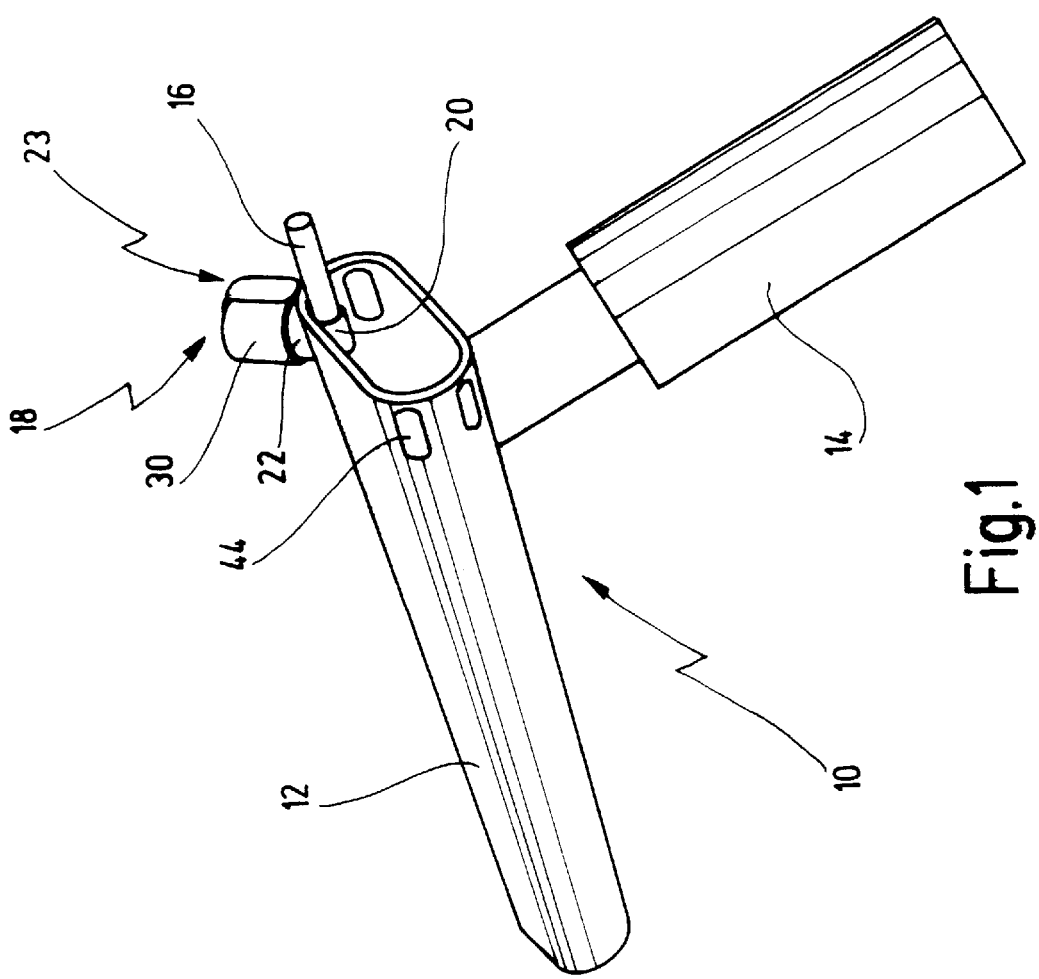
FIG. 1 shows a perspective view of a first embodiment of a medical instrument with a tubular shaft to which a rod-shaped element is secured with a fastening element.

An instrument 10 is illustrated in FIG. 1 having a shaft 12 as well a handle 14 attached thereto. The shaft 12 is formed as a tubular shaft. The instrument 10 here is a laryngoscope.

In this embodiment, a rod-shaped element 16 is a tubular shaft clamped to the inner wall of the shaft 12 with a fastening element 18 according to the present invention. The outer diameter of the hollow shaft is smaller than the inner diameter of the shaft 12. The rod-shaped element 16 is a flushing shaft in this case, however, it can also be a shaft for the optics of an endoscope or any other elongated element of arbitrary peripheral shape or cross section. The portion of the shaft to which the rod-shaped element 16 is clamped is the shaft 12 itself, more precisely the wall of the shaft 12.

Figure 2:
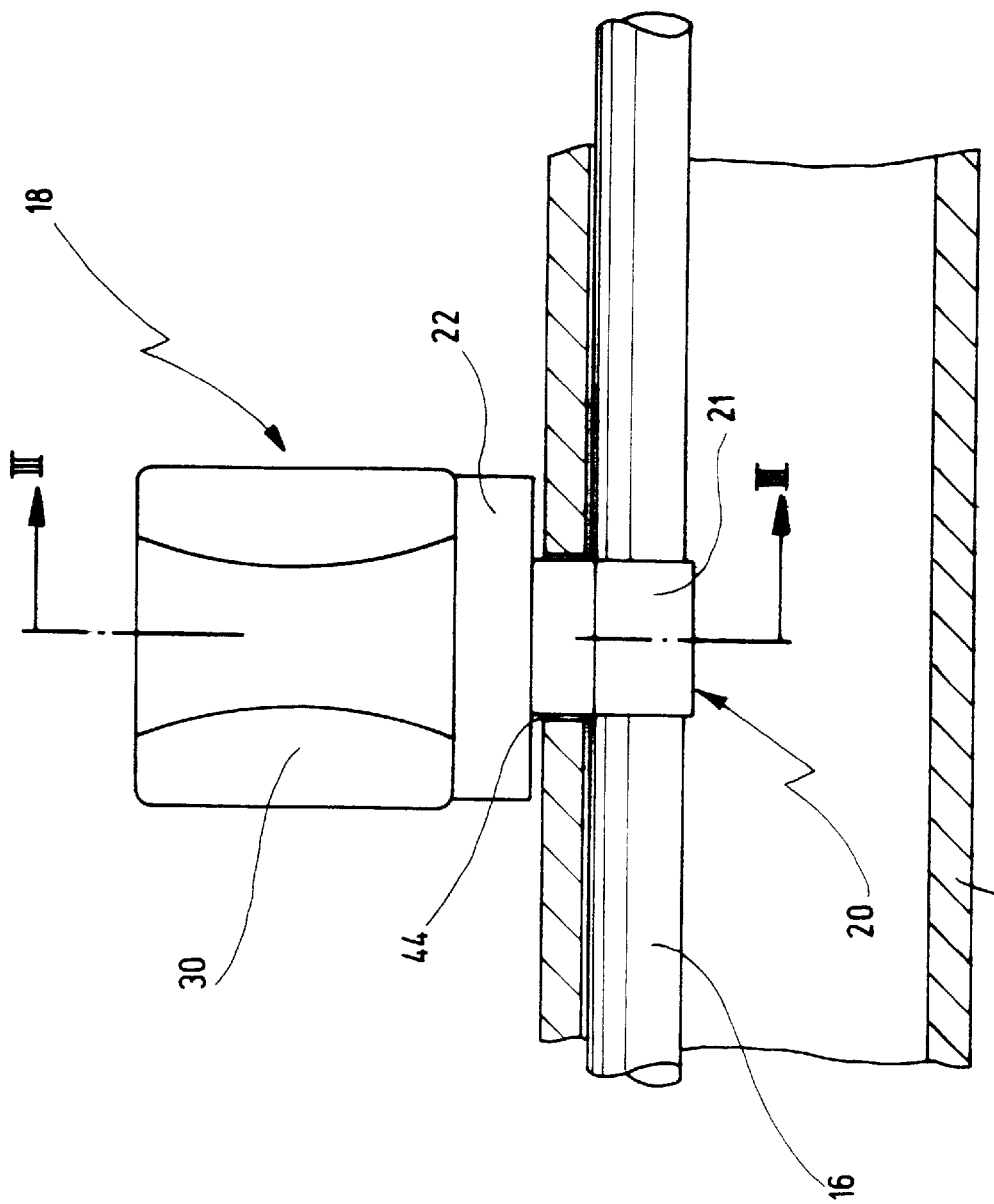
FIG. 2 shows a side view of an arrangement of the fastening element, the tubular shaft and a rod-shaped element fixed thereto with the fastening element.
Figure 3:
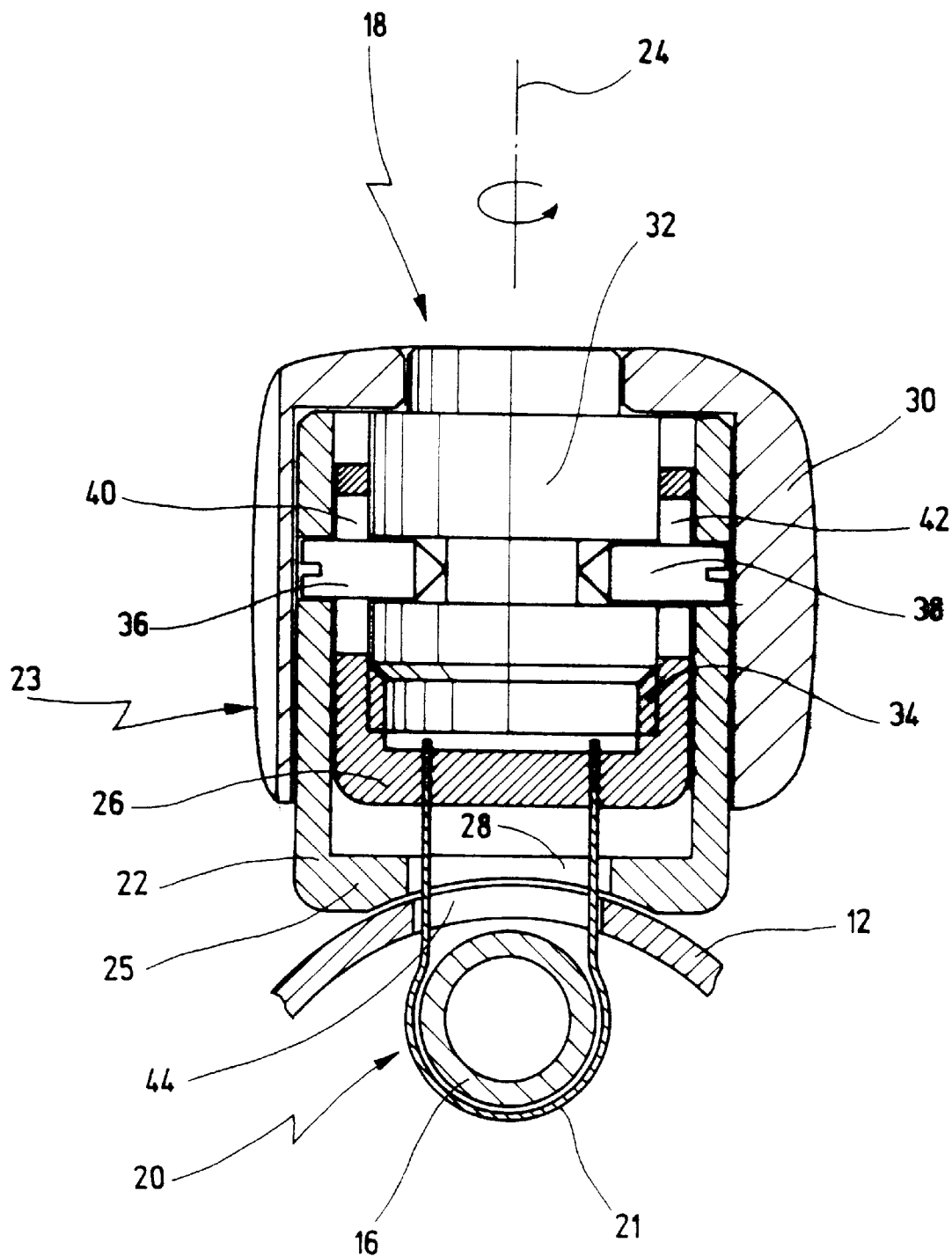
FIG. 3 shows a cross section along the line III—III in FIG. 2.

The fastening element 18, which can also be called a clamping adapter, will now be described in more detail with reference to FIGS. 1 to 3. The fastening element 18 comprises a bracket 20 having a radially elastic retainer section 21 at its lower end, which is expanded in the form of a section of a circle when seen in cross section.

The bracket 20 has a low material thickness. The bracket 20 can be formed for example as a flat metal band or a plastic band. The bracket 20 extends in longitudinal direction of the rod-shaped element 16 as can be seen in FIG. 2. Thus, it is formed as a wide band, for example with a width of 0.5 to 1 cm.

The fastening element 18 further comprises a tensioning mechanism 23, which when actuated draws the bracket 20 onto the inner wall of the shaft 12 for clamping the rod-shaped element 16 as will be described in more detail below. The bracket 20 is drawn continuously so that the clamping force is adjustable by the hand force of the user, independently of the cross sectional dimensions of the rod-shaped element 16. The tensioning mechanism 23 comprises a screw mechanism having an actuator element rotatable about a center axis 24 of the fastening element 18, where its rotation is converted into translational motion of the bracket 20 in the direction of the center axis 24, as will be described in detail below.

The fastening element 18 comprises a first stationary bushing 22, i.e. the first bushing 22 is neither axially shiftable with respect to the center axis 24 nor pivotal about the center axis 24. The first bushing 22 comprises a base portion 25 which in use engages with the outer wall of the shaft 12 as an abutment, namely in form-locking manner.

A second bushing 26 is arranged within the first stationary bushing 22, the bracket 20 being secured to its lower end. Bracket 20 is passed through an opening 28 in the base portion 25 of the first bushing 22 for this purpose. The second bushing 26 is non-rotatable about the center axis 24, however, it is axially moveable in the direction of the center axis 24. The bracket 20 is also non-rotatable due to the lack of rotation of the second bushing 26.

A turning knob 30 is arranged about the first stationary bushing 22 as an actuator element of the tensioning mechanism 23, which is rotatable about the center axis 24. The turning knob 30 is fixably connected with an inner pivot pin 32, i.e. when rotating the turning knob 30, the pivot pin 32 rotates in the same direction. The turning knob is part of the tensioning mechanism 23 and acts as actuator element for tightening or tensioning the fastening element 18.

The pivot pin 32 has an outer threading 34 at its lower end which engages with a corresponding inner threading in the second bushing 26. The first bushing 22 is locked against rotation by two screws 36, 38, which pass through vertical slotted holes 40, 42 and engage in an angular groove in the pin 32. The vertical length of the slotted holes 40, 42 corresponds to the axial displacement of the second bushing 26.

By turning the knob 30, the pivot pin 32 also rotates as mentioned. Through the engagement of the threadings between the pivot pin 32 and the second bushing 26, the pivot pin and with it the bracket 20 are moved upwardly and downwardly in the direction of the center axis 24 depending on the rotary direction of the turning knob 30.

The function of the fastening element 18 for securing a rod-shaped element 16 on the shaft 12 is described as follows:

A side opening 44 is formed in the shaft 12. In this case, the opening 44 is formed directly on the shaft 12 itself, i.e. the shaft portion is formed by a wall portion of the shaft 12 itself. The partially circular retainer section 21 of the bracket 20 has a diameter which is larger than the width of the opening 44, so that the bracket 20 is slightly elastically compressed when inserting the bracket through the opening 44 and expands elastically again when having passed through the opening 44. In this manner, the fastening element 18 is held like a catch or a clip in the opening 44 by the retainer section 21 of the bracket 20.

Four such side openings 44 are provided in the shaft 12 in FIG. 1 so that the fastening element 18 can be selectively placed in one of the openings 44. It is thus possible to clamp the rod-shaped element 16 at different peripheral positions on the shaft 12. Several fastening elements 18 can also be provided to secure correspondingly more rod-shaped elements 16 to the shaft 12. Several such openings 44 can also be distributed in longitudinal direction of the shaft 12 or the opening 44 can be formed as a slotted hole with corresponding axial extension, whose axis lies in the longitudinal direction of the shaft 12.

The fastening element 18 is placed in the open position by rotating the turning knob 30 before or after insertion through the opening 44. In this open position, the bracket 20 extends sufficiently out of the stationary bushing 22 to correspond to the diameter of the rod-shaped element 16.

The rod-shaped element 16 is then inserted into the partially circular section of the bracket 20. By turning the knob 30 in the opposite direction about the center axis 24, the bracket 20 is drawn onto the stationary bushing 22, i. e. in the direction out of the opening 44 of the shaft 12. The rod-shaped element 16 is drawn against the inner wall of the shaft 12 and clamped between the retainer section 21 and the inner wall, while the base portion 25 of the stationary bushing 22, having a curvature on its underside, forms an abutment against the tensioning forces from the bracket 20.

Thus, the bracket 20 can be tightened by turning the knob 30 until the rod-shaped element 16 is securely clamped to the tubular shaft 12. The inner shaft 16 is clamped to be free of deflection or tipping due to the axial extension of the bracket 20 in longitudinal direction of the tubular shaft 12.

A further embodiment of an instrument is shown in FIGS. 4 to 7 comprising a shaft 52 and a handle 54. In contrast to the shaft 12 of the instrument 10, the shaft 52 of the instrument 50 is not a tubular shaft, but formed as a shaft being open to the side. The fastening element 18 described in conjunction with FIGS. 1 to 3 can also be used with the instrument 50 to secure a rod-shaped element 56 to the shaft 52.

The location of securement for the instrument 50, however, is not on the shaft 52 itself, but on a portion of the shaft which is a holder 58 connected to the proximal end of the shaft 52. An opening 60 is provided in the holder 58 into which the bracket 20 of the fastening element 18 can be inserted as illustrated in FIGS. 4 to 7. The opening 60 is formed as a slotted hole which extends substantially over the entire length of the holder 58.

The holder 58 further comprises a section 62 curved with respect to the longitudinal direction of the shaft 52 and a straight section 54 running approximately parallel to the longitudinal direction of the shaft.

The configuration of the holder 58 with a curved section 62 and a straight section 64 makes it possible to secure the rod-shaped element 56 to the shaft 52 by corresponding positioning of the fastening element 18 at a certain axial location on the holder 58, so that the rod-shaped element 56 runs parallel to the longitudinal direction of the shaft 52 (FIG. 4) or has various angular orientations with respect to the longitudinal direction of the shaft 52, as illustrated in FIGS. 6 and 7.

In the embodiment shown in FIGS. 4 to 7, the fastening element 18 further comprises a counterplate 66 placed over the bracket 20 at the side of the opening 60 facing the rod-shaped element 56. The counterplate 66, which covers the opening 60 from the side facing the rod-shaped element 66, forms a defined abutment for the rod-shaped element 56. This is particularly advantageous when the holder element 58 is formed with a curved section 62.

Although the holder 58 is arranged at the proximal end of the shaft 52 in the illustrated embodiment, it is also contemplated to arrange the holder 58 at another position on the shaft 52.

It is also possible to provide the holder 58 to be removable from the shaft 52 and to provide it with a securement means, for example a clamping device, which allows the holder 58 to be removably secured to any arbitrary position on the shaft 52.

A slotted hole with a curved configuration as the opening 60 can also be directly integrated into the wall of the shaft 52 or be provided in the shaft of the instrument 10.

What is claimed is:

1. A fastening element for securing a rod-shaped element on a shaft of a medical instrument, comprising:

a bracket for engaging at least partially a circumference of said rod-shaped element, said bracket being insertable in a side opening of a shaft portion of said shaft;

a tensioning mechanism which when actuated draws said bracket in a direction out of said opening for clamping said rod-shaped element onto said shaft portion, wherein said tensioning mechanism is configured such that the clamping force of said tensioning mechanism for clamping said rod-shaped element is continuously adjustable when actuating said tensioning mechanism.

2. The fastening element of claim 1, wherein said tensioning mechanism comprises a screw mechanism having an actuator element rotatable about a center axis of said fastening element, whose rotary motion is converted into a motion of said bracket in an axial direction of said fastening element.

3. The fastening element of claim 2, wherein said tensioning mechanism comprises a retainer for said bracket moveable in said axial direction of said fastening element, to which said bracket is secured and which is connected to said actuator element by engagement of a threading.

4. The fastening element of claim 3, wherein said tensioning mechanism comprises a turning knob enclosing a first non rotatable bushing, said bushing having a base portion provided with an opening for said bracket passing there through, whose outer side engages with said shaft portion, wherein said first bushing surrounds said retainer configured as a second bushing and wherein said turning knob is fixedly connected to a pivot pin extending through said retainer, which engages with said retainer through a threading.

5. The fastening element of claim 1, further comprising an abutment adapted to receive a contour of said shaft portion in substantially form-locking manner.

6. The fastening element of claim 1, wherein said bracket comprises a radially elastic retainer section formed to be partially circularly expanded into which said rod-shaped element can be inserted, said retainer section having a diameter larger than a transverse dimension of said opening in said shaft portion.

7. The fastening element of claim 1, wherein said bracket has a small material thickness.

8. The fastening element of claim 1, wherein said bracket extends over a partial length in a longitudinal direction of said rod-shaped element.

9. The fastening element of claim 1, wherein a counterplate is provided on said bracket at the side of said opening facing the rod-shaped element.

10. A medical instrument, comprising:

a shaft having at least one side opening in a shaft portion of said shaft;

a fastening element for securing a rod-shaped element on said shaft, said fastening element further comprising:

a bracket for engaging at least partially a circumference of said rod-shaped element; said bracket being insertable in said side opening of said shaft portion of said shaft;

a tension mechanism which when actuated draws said bracket in a direction out of said opening for clamping said rod-shaped element onto said shaft portion, wherein said tensioning mechanism is configured such that the clamping force of said tensioning mechanism for clamping said rod-shaped element is continuously adjustable when actuating said tensioning mechanism.

11. The medical instrument of claim 10, wherein said tensioning mechanism comprises a screw mechanism having an actuator element rotatable about a center axis of said fastening element, whose rotary motion is converted into a motion of said bracket in an axial direction of said fastening element.

12. The medical instrument of claim 11, wherein said tensioning mechanism comprises a retainer for said bracket moveable in said axial direction of said fastening element, to which said bracket is secured and which is connected to said actuator element by engagement of a threading.

13. The medical instrument of claim 12, wherein said tensioning mechanism comprises a turning knob enclosing a first non-rotatable bushing, said bushing having a base portion provided with an opening for said bracket passing there through, whose outer side engages with said shaft portion, wherein said first bushing surrounds said retainer configured as a second bushing and wherein said turning knob is fixedly connected to a pivot pin extending through said retainer, which engages with said retainer through a threading.

14. The medical instrument of claim 10, further comprising an abutment adapted to receive a contour of said shaft portion in substantially form-locking manner.

15. The medical instrument of claim 10, wherein said bracket comprises a radially elastic retainer section formed to be partially circularly expanded into which said rod-shaped element can be inserted, said retainer section having a diameter larger than a transverse dimension of said opening in said shaft portion.

16. The medical instrument of claim 10, wherein said bracket has a small material thickness.

17. The medical instrument of claim 10, wherein said bracket extends over a partial length in a longitudinal direction of said rod-shaped element.

18. The medical instrument of claim 10, wherein a counter-plate is provided on said bracket at the side of said opening facing the rod-shaped element.

19. The medical instrument of claim 10, wherein said shaft portion is formed by a wall of said shaft itself.

20. The instrument of claim 10, wherein said shaft portion is a holder connected to said shaft.

21. The instrument of claim 20, wherein said holder is releasable from said shaft.

22. The instrument of claim 10, wherein said shaft portion is a holder connected to said shaft and said holder can be secured at various positions on said shaft.

23. The instrument of claim 10, wherein said opening is formed as a slotted hole whose axis extends in longitudinal direction of said shaft.

24. The instrument of claim 10, wherein a plurality of openings are formed to be distributed on said shaft portion.

25. The instrument of claim 10, wherein said shaft portion comprises at least partially a curved section being curved with respect to the longitudinal direction of said shaft and wherein said opening is formed as a slotted hole which at least extends over said curved section of said shaft portion.

* * * * *